(12) United States Patent
Zimmerman

(10) Patent No.: US 12,048,441 B2
(45) Date of Patent: Jul. 30, 2024

(54) ORTHOPEDIC BROACH

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventor: Jacob Zimmerman, Memphis, TN (US)

(73) Assignees: Smith & Nephew, Inc.; Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 573 days.

(21) Appl. No.: 17/323,657

(22) Filed: May 18, 2021

(65) Prior Publication Data

US 2021/0361296 A1 Nov. 25, 2021

Related U.S. Application Data

(60) Provisional application No. 63/028,168, filed on May 21, 2020.

(51) Int. Cl.
*A61B 17/16* (2006.01)
*A61B 90/00* (2016.01)
*A61B 17/00* (2006.01)

(52) U.S. Cl.
CPC ...... *A61B 17/1659* (2013.01); *A61B 17/1613* (2013.01); *A61B 90/03* (2016.02); *A61B 2017/00477* (2013.01)

(58) Field of Classification Search
CPC .............. A61B 17/1659; A61B 17/164; A61B 17/1668; A61B 17/1664
See application file for complete search history.

(56) References Cited

U.S. PATENT DOCUMENTS

| | | | |
|---|---|---|---|
| 5,350,381 A | 9/1994 | Melton | |
| 6,663,636 B1 | 12/2003 | Lin | |
| 8,657,834 B2 * | 2/2014 | Burgi | A61B 17/1659 606/99 |
| 10,568,644 B2 | 2/2020 | Tsukayama et al. | |

FOREIGN PATENT DOCUMENTS

EP 2777551 A1 9/2014

\* cited by examiner

*Primary Examiner* — Andrew Yang
(74) *Attorney, Agent, or Firm* — KDW Firm PLLC

(57) ABSTRACT

An orthopedic broach is disclosed. The orthopedic broach includes a cutting tip and a broach handle. The broach handle includes a lever, a spring, and a latch. The lever is movably coupled to the handle and to an end of the spring. The latch is movably coupled to the handle and the opposite end of the spring. In use, the lever is movable from an opened position, where the latch is positioned in a released position, so that the cutting tip can be inserted into the handle, to a closed position where the latch is moved to an engaged position wherein the cutting tip is securely coupled to the latch, and thus the handle. The handle includes a spring stop to prevent the spring from further deflection to prevent the latch from moving to the released position and thus prevent decoupling of the cutting tip when excessive forces are applied.

20 Claims, 5 Drawing Sheets

ORTHOPEDIC BROACH

CROSS-REFERENCE TO RELATED APPLICATIONS

This is a non-provisional of, and claims the benefit of the filing date of, U.S. provisional patent application No. 63/028,168, filed May 21, 2020, entitled "Orthopedic Broach," the entirety of which application is incorporated by reference herein.

FIELD OF THE INVENTION

The present disclosure is directed to orthopedic instruments such as, an orthopedic broach, and more particularly, to an improved linkage or coupling mechanism for coupling a broach or cutting tip to a handle to prevent the broach or cutting tip from loosening or breaking away from the handle.

BACKGROUND

Orthopedic instruments such as, for example, an orthopedic broach, rasp, cutting instrument, etc. (terms used interchangeably herein without the intent to limit) are well known. In use, a broach is used during, for example, hip arthroplasty surgeries. In use, the surgeon uses the broach to prepare an inner surface of a patient's intramedullary canal to receive an orthopedic implant such as, for example, a femoral hip prosthesis. The preparation of the intramedullary canal by the surgeon is designed to insure a proper fit between the patient's femur and the hip prosthesis.

One well-known broach design includes a broach (or cutting tip), a handle including a lever, and a spring used to couple the broach to the handle. For example, U.S. Pat. No. 6,663,636 to Lin entitled "Femur Rasp Fastener" discloses a broach or rasp comprising a frame or handle, and a linkage means. The frame has a chamber formed therein to house at least a portion of the linkage means and a front end having an anchor opening to couple, receive, etc. an end portion of the rasp or broach. The linkage means includes a handle or lever, an elastic suspension bar or leaf spring, and a bucking head or latch.

In use, the handle is moved upwards to retract the bucking head. With the bucking head retracted, a portion of the rasp can be inserted into the anchor opening formed in the front end of the frame. The handle is then moved in the opposite direction to move the suspension bar forward, which in turn moves the bucking head forward such that the bucking head engages a recess formed in the portion of the rasp inserted into the anchor opening formed in the front end of the frame.

A disadvantage with the current design is that over time, the suspension bar or spring may become worn thus decreasing the amount of resistance provided to the bucking head or latch (e.g., thereby making it more likely that the rasp can be decoupled from the frame or handle). In addition, and/or alternatively, broach handles that rely on a suspension bar or spring to couple the broach to the handle can disassociate from the broach during extraction of the broach from the patient's intramedullary canal if the extraction force applied to the broach handle is greater than the spring force. That is, during removal of the broach from the patient's intramedullary canal, the broach may become struck within the patient's intramedullary canal. In response, a surgeon may strike the backside of the broach handle to remove or pull the broach from the patient's intramedullary canal. However, if the force applied to the broach handle is too great, the broach handle can disconnect from the broach leaving the broach in the patient's intramedullary canal (e.g., application of a large extraction force can cause the broach to release from the bucking head or latch).

Thus, there remains a need to provide an improved linkage or coupling mechanism for coupling the broach to the handle (e.g., an improved linkage or coupling mechanism that prevents, or at least greatly minimizes, the broach decoupling from the handle). The present invention satisfies this need and provides other benefits and advantages in a novel and unobvious manner.

BRIEF SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In one embodiment, an orthopedic broach is disclosed. In use, the orthopedic broach includes a broach or cutting tip and a broach handle. The broach handle includes a lever, a spring, and a latch. The lever is arranged and configured to move relative to the handle (e.g. lever is movably or pivotably coupled to the handle). Similarly, the latch is arranged and configured to move relative to the handle (e.g., latch is movably or pivotably coupled to the handle). The spring couples the lever to the latch. In one embodiment, the spring includes first and second ends, the first end is arranged and configured to couple to the lever (e.g., the first end of the spring is movably or pivotably coupled to the lever). The second end is arranged and configured to couple to the latch (e.g., the second end of the spring is movably or pivotably coupled to the latch). In use, the lever is movable (e.g. pivotable) from a first or opened position to a second or closed position. Similarly, the latch is movable (e.g. pivotable) from a first or released position to a second or engaged position. With the lever in the first or opened position, the latch is positioned in the first or released position so that the broach can be inserted into the handle. With the lever in the second or closed position, the latch is in the second or engaged position wherein the broach is securely engaged to the latch, and thus the handle.

In one embodiment, the handle includes a spring stop (e.g., a stop member) arranged and configured to contact the spring to prevent further bowing, deflection, or movement (terms used interchangeably herein without the intent to limit) of the spring. That is, with the lever in the second or closed position, the handle includes a spring stop arranged and configured to contact the spring to prevent further deflection or movement of the spring to prevent the latch from moving to the second or released position, and thus preventing the broach from decoupling from the latch when excessive forces are applied to the orthopedic broach.

In one embodiment, the spring stop is an inner wall of the handle arranged and configured to prevent excessive deflection or movement of the spring.

In one embodiment, an orthopedic broach is disclosed. The orthopedic broach including a cutting tip and a handle including a lever, a spring, and a latch. The lever is moveably coupled to the handle between a first position and a second position. The latch is moveably coupled to handle between a released position and an engaged position. The spring couples the lever to the latch so that movement of the lever from the first position to the second position moves the latch from the released position wherein the cutting tip can be inserted into the handle to the engaged position wherein the cutting tip is coupled to the latch. The handle further includes a stop member arranged and configured to contact the spring so that in the second position, the stop member contacts the spring to prevent further deflection of the spring to provide increased resistance against removal of the cutting tip from the latch.

In one embodiment, by preventing further deflection of the spring, the stop member increases a total resistance provided by the spring to prevent decoupling of the cutting tip from the handle when excessive forces are applied to the orthopedic broach.

In one embodiment, the stop member is arranged and configured as an inner wall of the handle.

In one embodiment, the stop member is arranged and configured as a screw arranged and configured to extend through an opening formed in the handle and into contact with the spring, rotation of the screw adjusting a deflection of the spring.

In one embodiment, the spring includes first and second ends, the first end is coupled to the lever, the second end is coupled to the latch.

In one embodiment, the cutting tip includes a connector portion at an end thereof, the connector portion including a recess arranged and configured to receive a tip of the latch.

In one embodiment, moving the lever from the first position to the second position causes the spring to move the latch into engagement with the recess formed in the connector portion of the cutting tip to secure the cutting tip to the handle.

In one embodiment, moving the lever from the first position to the second position causes the spring to deflect from a first unflexed position to a second flexed position, the stop member preventing the spring from completely flexing thereby providing an increased force onto the latch to prevent the latch from moving to the released position.

In one embodiment, the lever and the latch are pivotably coupled to the handle.

In one embodiment, the lever is pivotably coupled to the handle via a first pivot pin passing through the lever, the latch is pivotably coupled to the handle via a second pivot pin passing through the latch, the spring includes a first end and a second end, the first end of the spring is pivotably coupled to the lever by a third pivot pin, and the second end of the spring is pivotably coupled to the latch via a fourth pivot pin.

In one embodiment, with the lever in the first position, the spring is in an unflexed position extending between the lever and the latch, and, with the lever in the second position, the spring transitions to a flexed position to exert an increased force onto the latch, the stop member preventing the spring from unflexing in the second position and thus preventing the latch from releasing the cutting tip.

In one embodiment, an orthopedic broach is disclosed. The orthopedic broach including a cutting tip, a handle, and means for preventing the linkage from moving in the second position. The handle includes a lever, a linkage, and a latch. The lever is moveably coupled to the handle between a first position and a second position. The latch is moveably coupled to handle between a released position and an engaged position. The linkage couples the lever to the latch so that movement of the lever from the first position to the second position moves the latch from the released position wherein the cutting tip can be inserted into the handle to the engaged position wherein the cutting tip is coupled to the latch. The means for preventing the linkage from moving in the second position operates so that, in the second position, the latch is subjected to increased resistance from moving to prevent the cutting tip from being decoupled from the handle.

In one embodiment, the linkage is a spring arranged and configured to move between a first configuration and a second configuration, the spring comprising increased flexion in the second configuration. Movement of the lever from the first position to the second position, transitions the spring from the first configuration to the second configuration. The means for preventing the linkage from moving restricts an amount of flexion of the spring in the second configuration.

In one embodiment, the means for preventing the linkage from moving comprises a stop surface arranged and configured to contact the spring in the second position to restrict the amount of flexion of the spring.

In one embodiment, the stop member increases a total resistance provided by the spring to prevent decoupling of the cutting tip from the handle when excessive forces are applied to the orthopedic broach.

In one embodiment, the stop surface is arranged and configured as an inner wall of the handle.

In one embodiment, the cutting tip includes a connector portion at an end thereof, the connector portion including a recess arranged and configured to receive a tip of the latch.

In one embodiment, moving the lever from the first position to the second position causes the linkage to deflect from a first unflexed position to a second flexed position, the means for preventing the linkage from moving inhibiting the linkage from completely flexing thereby providing an increased force onto the latch to prevent the latch from moving to the released position.

In one embodiment, the lever and the latch are pivotably coupled to the handle.

In one embodiment, the lever is pivotably coupled to the handle via a first pivot pin passing through the lever, the latch is pivotably coupled to the handle via a second pivot pin passing through the latch, the linkage includes a first end and a second end, the first end of the linkage is pivotably coupled to the lever by a third pivot pin, and the second end of the linkage is pivotably coupled to the latch via a fourth pivot pin.

In one embodiment, the linkage is a leaf spring, and, with the lever in the first position, the spring is in an unflexed position extending between the lever and the latch, and, with the lever in the second position, the spring transitions to a flexed position to exert an increased force onto the latch, the means for preventing the linkage from moving being arranged and configured to prevent the spring from unflexing in the second position and thus preventing the latch from releasing the cutting tip.

Embodiments of the present disclosure provide numerous advantages. For example, by incorporating one or more features of the present disclosure, in use, the spring coupling the lever to the latch, and hence the broach to the handle, is prevented from further bending, bowing, deflecting, moving, etc. prior to the point where the latch releases the broach. Thus arranged, the spring prevents the latch from moving to the second or released position, and thus prevents the broach from decoupling from the handle when subjected to excessive removal forces. In use, the spring provides increased resistance to decoupling of the broach from the handle.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which.

Figure 1:
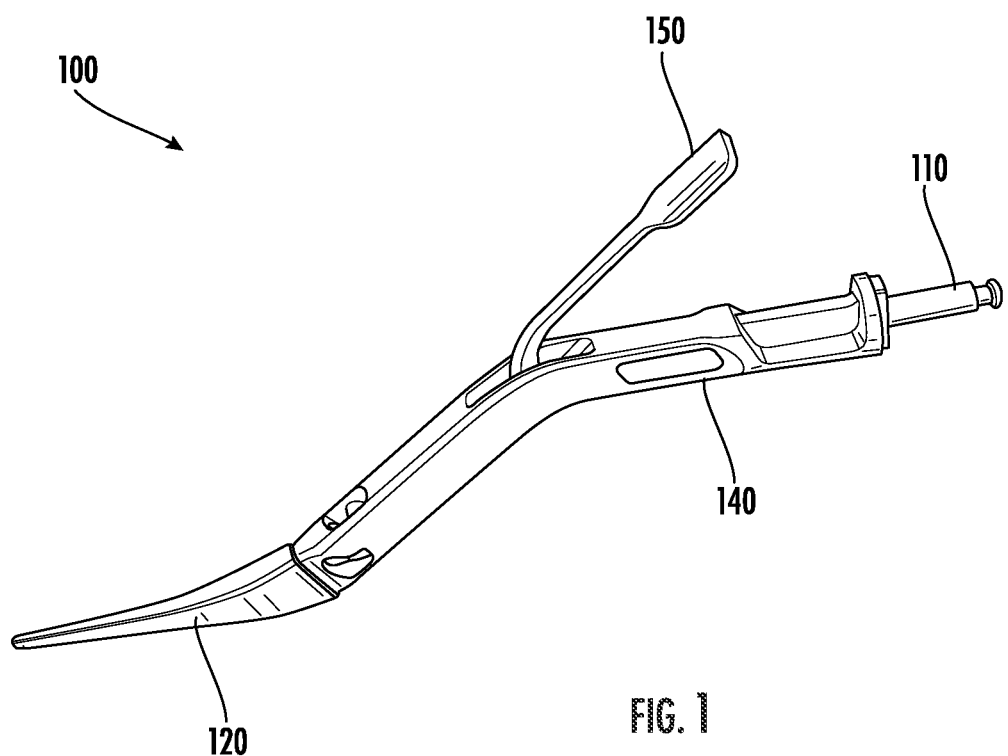
FIG. 1 is a perspective view of an example of an embodiment of an orthopedic broach in accordance with one or more features of the present disclosure.
Figure 2:
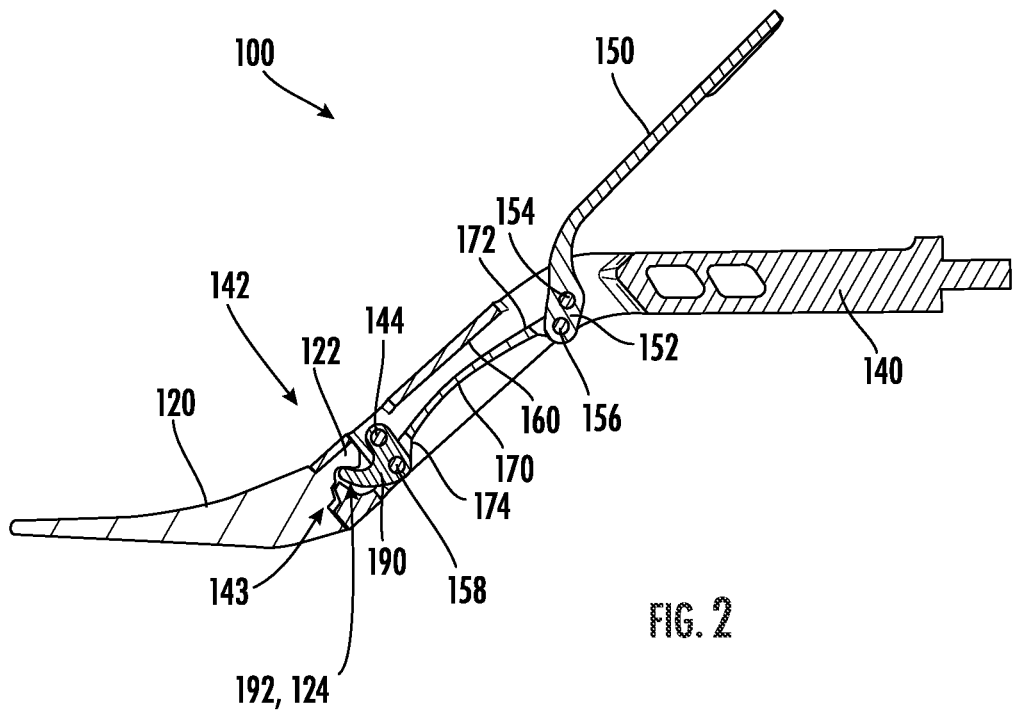
FIG. 2 is a detailed, cross-section view of the orthopedic broach shown in FIG. 1, the orthopedic broach illustrated in a first or released position.
Figure 3:
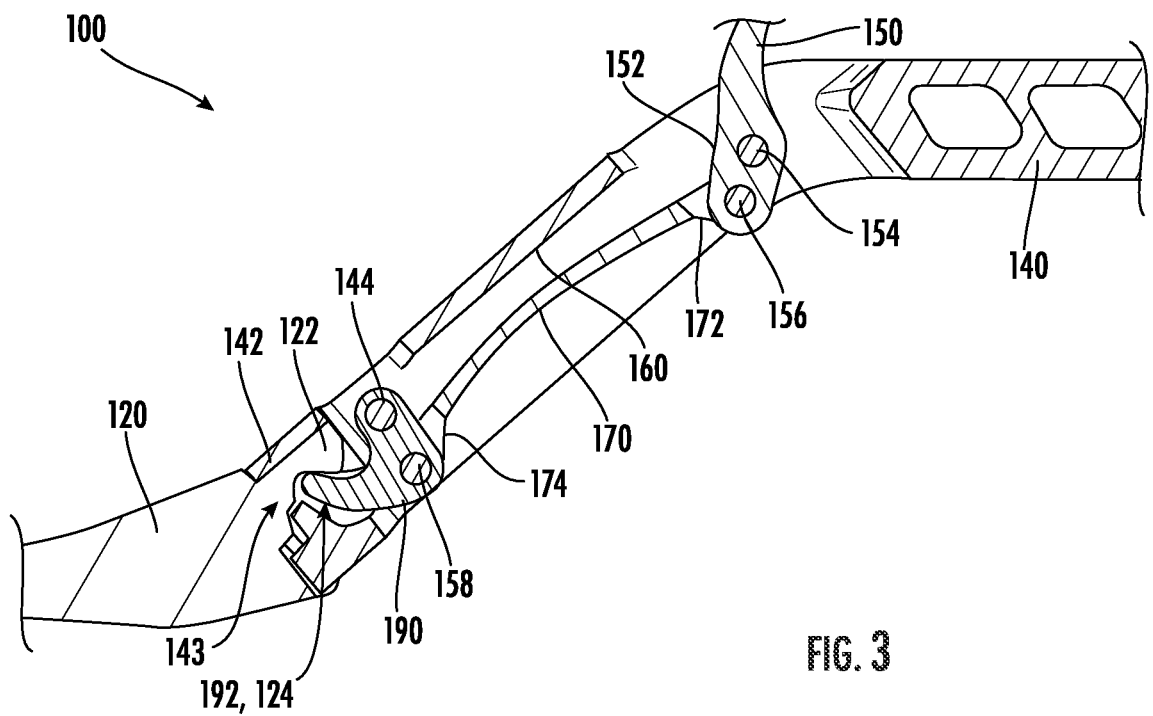
FIG. 3 is a detailed, cross-sectional view of a linkage or coupling mechanism of the orthopedic broach as shown in FIG. 2.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein. In the drawings, like numbers refer to like elements throughout unless otherwise noted.

DETAILED DESCRIPTION

Various features or the like of orthopedic broaches will now be described more fully hereinafter with reference to the accompanying drawings, in which one or more features of the orthopedic broaches will be shown and described. It should be appreciated that the various features or the like may be used independently of, or in combination, with each other. It will be appreciated that an orthopedic broach as disclosed herein may be embodied in many different forms and should not be construed as being limited to the embodiments set forth herein. Rather, these embodiments are provided so that this disclosure will convey certain features of the orthopedic broach to those skilled in the art.

Disclosed herein is an orthopedic instrument such as, for example, an orthopedic broach including one or more features arranged and configured to provide an improved linkage or coupling mechanism for coupling a broach or cutting tip to a handle. More specifically, in accordance with one or more features of the present disclosure, the linkage or coupling mechanism is arranged and configured to provide increased resistance to prevent the broach or cutting tip from releasing or decoupling from the handle during removal such as, for example, as may occur during a hip surgery. While the present disclosure will be illustrated and described in connection with an orthopedic broach, the linkage or coupling mechanism can be used to hold any number of medical devices for insertion and/or removal, including many different types of implants, trials, and other instruments that require a holding device. As such, the present disclosure should not be limited to an orthopedic broach unless explicitly claimed.

Referring to FIGS. 1-6, an example of an embodiment of an orthopedic broach 100 in accordance with one or more features of the present disclosure is illustrated. In use, as previously mentioned, the orthopedic broach 100 is arranged and configured to prepare an inner surface of a patient's intramedullary canal to receive an orthopedic implant such as, for example, a femoral hip prosthesis. For example, the orthopedic broach 100 may be coupled to an orthopedic impactor, which is arranged and configured to accurately and safely apply a driving force to the orthopedic broach 100 to prepare an intramedullary canal of a patient's bone. In addition, the orthopedic impactor may be arranged and configured to apply a reverse force to the orthopedic broach 100 to remove the orthopedic broach from the patient's bone. As illustrated, in one embodiment, the orthopedic broach 100 includes a coupling mechanism 110 for coupling to, for example, the orthopedic impactor. The coupling mechanism 110 may have a quick connect mechanism to facilitate rapid change, however, the coupling mechanism 110 may be any suitable coupling mechanism now known or hereafter developed.

In one embodiment, as illustrated, the orthopedic broach 100 may also include a broach or cutting tip 120 and a handle or frame 140 (terms used interchangeably herein without the intent to limit). The handle 140 includes a lever 150, a spring 170, and a latch 190. The latch 190 is arranged and configured to engage a connector portion 122 of the broach 120. The spring 170 is arranged and configured to couple the lever 150 and the latch 190 so that, in use, movement of the lever 150 from the first or opened position (FIGS. 2 and 3) to the second or closed position (FIGS. 4 and 5) moves the spring 170, which moves the latch 190 into engagement with the connector portion 122 of the broach 120). FIG. 6 illustrates the first or opened position of FIGS. 2 and 3 juxtaposed onto the second or closed position of FIGS. 4 and 5 to better demonstrate how the spring 170 and the latch 190 move in response to moving the lever 150 between the first and second positions.

Figure 4:
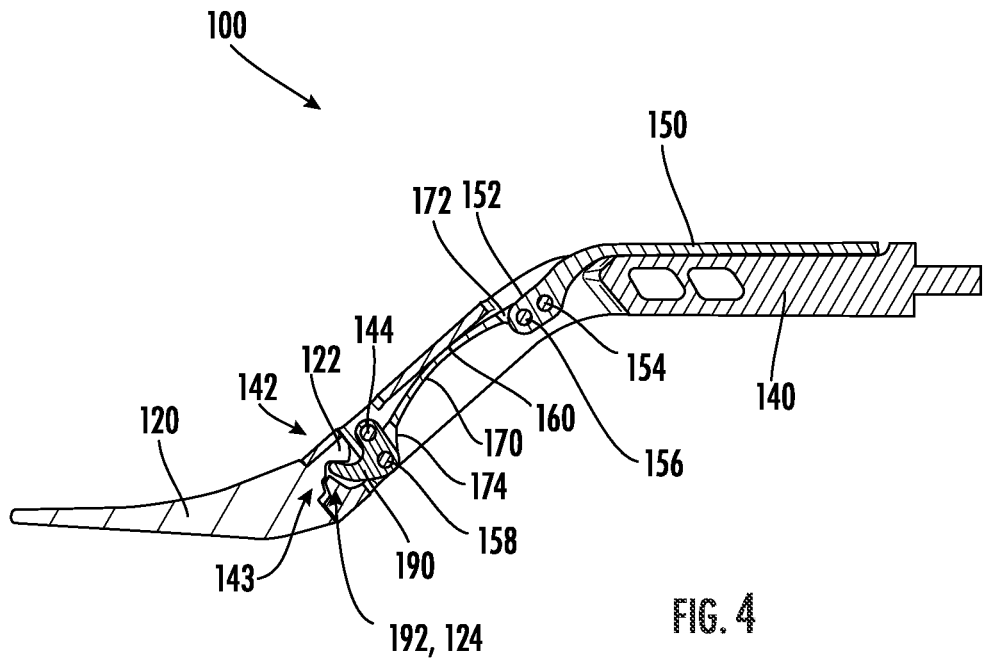
FIG. 4 is a cross-section view of the orthopedic broach shown in FIG. 1, the orthopedic broach illustrated in a second or engaged position.
Figure 5:
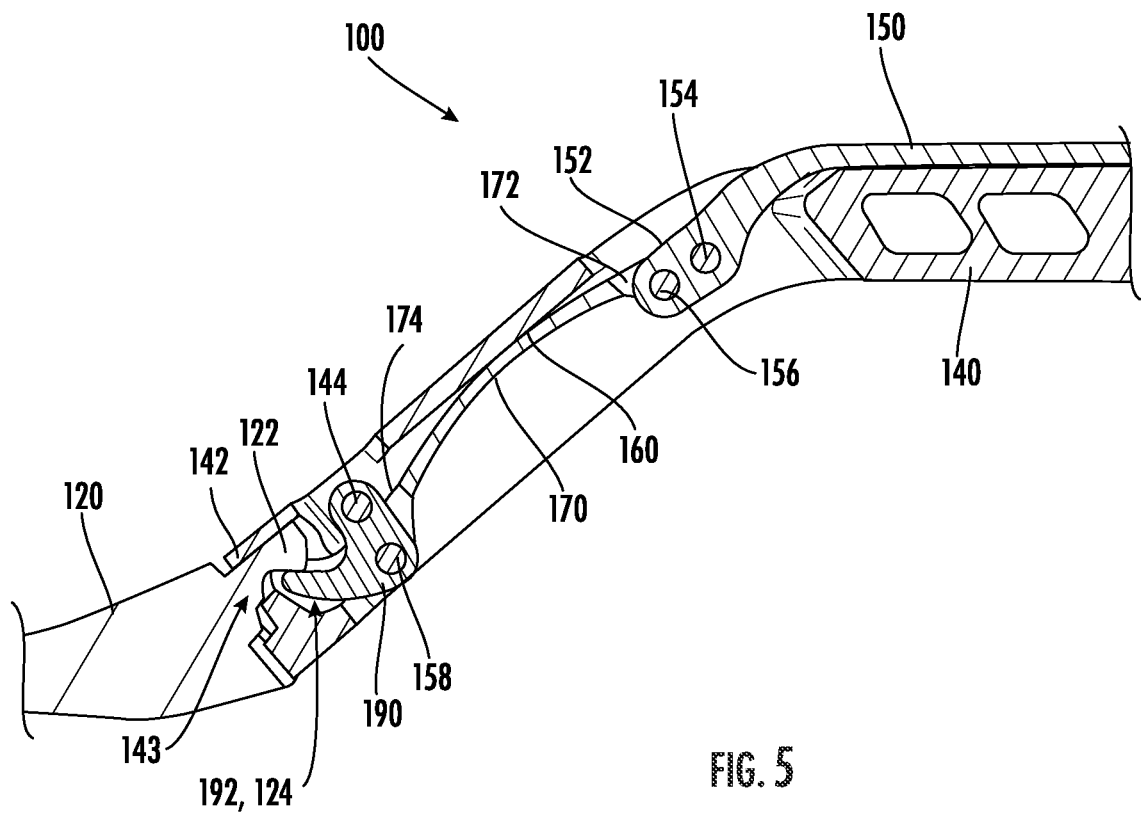
FIG. 5 is a detailed view of a linkage or coupling mechanism of the orthopedic broach as shown in FIG. 4.
Figure 6:
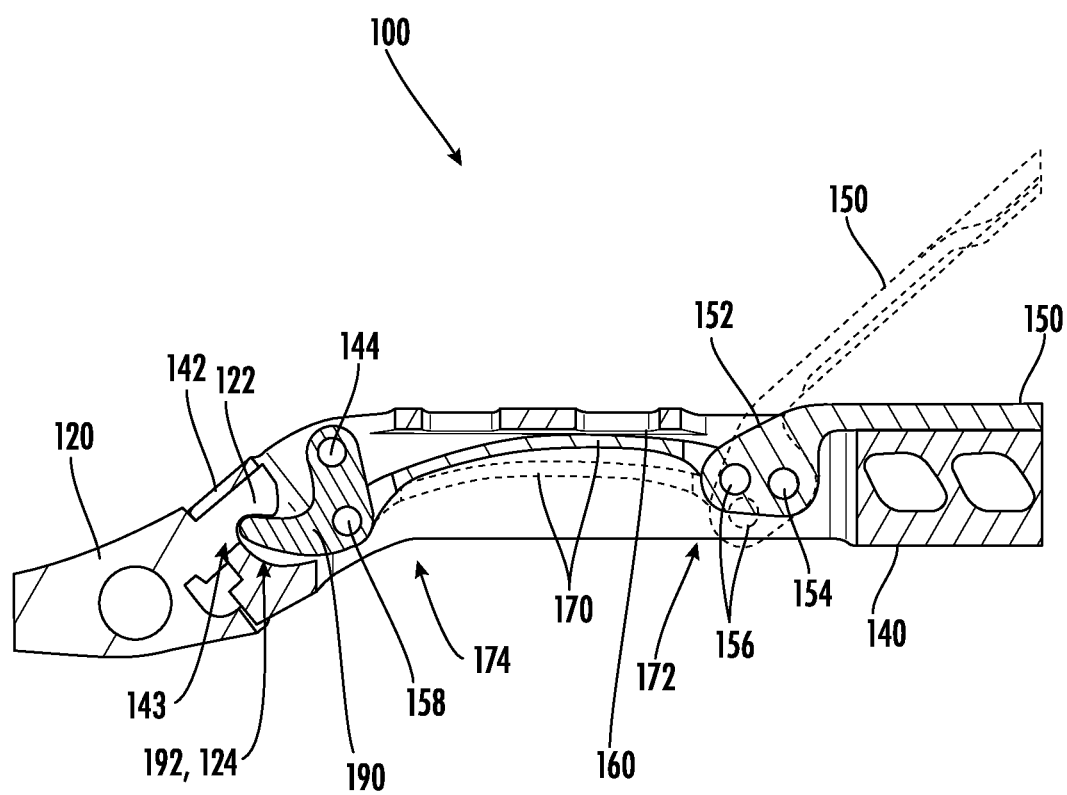
FIG. 6 is a cross-section view of the orthopedic broach shown in FIG. 1, the orthopedic broach shown with the second or engaged position juxtapose over the second or released position.

That is, in use, as will be described in greater detail herein, the lever 150 is movable between a first or opened position (FIGS. 2 and 3) and a second or closed position (FIGS. 4 and 5). In use, with the connector portion 122 of the broach 120 inserted into an opening 143 formed in a distal end 142 of the handle 140, the lever 150 is moved from the first or opened position (FIGS. 2 and 3) to the second or closed position (FIGS. 4 and 5) causing the spring 170 to move forward pressing the latch 190 into further engagement with the connector portion 122 of the broach 120 to secure the broach 120 to the handle 140.

In accordance with one or more features of the present disclosure, and in contrast to known orthopedic broaches, the spring 170 is prevented from completely flexing as the lever 150 is moved from the first or opened position (FIGS. 2 and 3) to the second or closed position (FIGS. 4 and 5). Thus arranged, the spring 170 is arranged and configured to apply an additional force to maintain the coupling between the broach 120 and the handle 140 (e.g., by preventing the spring 170 from fully flexing, the spring 170 continues to provide an increased force to the latch 190 thereby preventing the latch 190 from moving and thus preventing releasing the connector portion 122 of the broach 120). That is, in connection with known orthopedic broaches such as disclosed in U.S. Pat. No. 6,663,636 to Lin, when the lever or handle is moved from the first or opened position to the second or closed position, the spring flexes forcing the spring to hold the broach to the handle. However, if a large enough force is applied, the broach will decouple from the handle. In contrast, in accordance with one or more features of the present disclosure, by preventing the spring 170 from fully flexing, the latch 190 is prevented from releasing the broach 120.

Referring to FIGS. 1-6, in one embodiment, the orthopedic broach 100 includes a broach (e.g., a cutting tip) 120. In one embodiment, the broach 120 includes a connector portion, a projection, a stem, etc. 122 (terms used interchangeably herein without the intent to limit). The connector portion 122 is arranged and configured to be received within, inserted, etc. into an opening 143 formed in a distal end 142 of the handle 140. As illustrated, and as will be described, the connector portion 122 includes a recess 124 arranged and configured to receive an end portion or tip 192 of the latch 190.

As further illustrated, the lever 150 is pivotably coupled to the handle 140 so that the lever 150 is movable from a first or opened position (FIGS. 2 and 3) to a second or closed position (FIGS. 4 and 5). In one embodiment, the lever 150 may be pivotably coupled to the handle 140 via a pivot pin 154 passing through a distal end 152 of the lever 150, although other mechanisms for movable coupling the lever 150 to the handle 140 are envisioned.

Similarly, the latch 190 is pivotably coupled to the handle 140 so that the latch 190 is movable from a first or released position (FIGS. 2 and 3) to a second or engaged position (FIGS. 4 and 5). In the first or released position, the latch 190 is able to move so that a user can insert the connector portion 122 of the broach 120 through the opening 143 formed in the distal end 142 of the handle 140. In the second or engaged position, with the broach 120 properly inserted, the latch 190 is pressed into further engagement with the connector portion 122 of the broach 120 to thereby prevent its release (e.g., end portion or tip 192 of the latch 190 is pressed into the recess 124 formed in the connector portion 122 of the broach 120 thereby securely coupling the broach 120 to the handle 140). In one embodiment, the latch 190 may be pivotably coupled to the handle 140 via a pivot pin 144 passing through the latch 190, although other mechanisms for movable coupling the latch 190 to the handle 140 are envisioned.

As illustrated, in one embodiment, the spring 170 includes a first end 172 and a second end 174. The first end 172 being pivotably coupled to the lever 150. The second end 174 being pivotably coupled to the latch. As illustrated, in one embodiment, the spring 170 may be pivotably coupled to the lever 150 via a pivot pin 156 passing through a distal end 152 of the lever 150. The spring 170 may be pivotably coupled to the latch 190 via a pivot pin 158 passing through the latch 190. Although other mechanisms for movable coupling the spring 170 to the latch 190 and lever 150 are envisioned.

In use, with the lever 150 in the first or opened position (FIGS. 2 and 3), the spring 170 is in an unflexed position extending between the lever 150 and the latch 190, which is in the first or released position. Thus arranged, the connector portion 122 of the broach 120 can be inserted into the opening 143 formed in the distal end 142 of the handle 140 so that the end portion or tip 192 of the latch 190 engages the recess 124 formed in the connector portion 122 of the broach 120. In use, with the broach 120 properly positioned, the lever 150 is moved (e.g., pivoted) from the first or opened position (FIGS. 2 and 3) to the second or closed position (FIGS. 4 and 5), which causes the spring 170 to move forward or distally causing the spring 170 to exert an increased force to the latch 190 causing the latch 190 to move from the first or released position to the second or engaged position to securely engage the end portion or tip 192 with the recess 124 formed in the connector portion 122 of the broach 120.

That is, in one embodiment, as illustrated, moving the lever 150 from the first or opened position (FIGS. 2 and 3) to the second or closed position (FIGS. 4 and 5), causes the spring 170 to bow, deflect, or bend upwards, although it is envisioned that the spring 170 may be configured so that moving the lever 150 to the second or closed position causes the spring 170 to bow, deflect, or bend downwards. Generally speaking, in normal use, flexing of the spring 170 causes the spring 170 to reach a position where it achieves its shortest distance (e.g., as measured between the first and second ends 172, 174 thereof). However, continued movement of the lever 150 causes the spring 170 to begin to slightly open/expand. In use, the slight expansion of the spring 170 causes the lever 150 to be biased to the closed position (FIGS. 4 and 5) so that the user does not need to hold the lever 150 in the closed position (FIGS. 4 and 5).

In accordance with one or more features of the present disclosure, the spring 170 is prevented from fully deflecting. That is, the handle 140 may be arranged and configured with a spring stop 160 arranged and configured to prevent the spring 170 from further deflecting. Thus arranged, the spring stop 160 can be positioned to ensure that the spring 170 applies an increased level of force or resistance to the latch 190 thereby preventing the latch 190 from moving and thus preventing the broach 120 from decoupling from the latch 190. That is, in use, the increased resistance occurs when the broach 120 is pulled away from the handle 140, thus moving the latch 190 and deflecting the spring 170. In accordance with principles of the present disclosure, when the spring 170 hits the spring stop 160, the resistance to deflection is increased.

In use, the spring stop 160 may be arranged and configured to prevent the spring 170 from further deflecting by any suitable mechanism now known or hereafter developed. For example, the handle 140 can be arranged and configured with an inner wall or surface designed to contact the spring 170 to prevent further deflection (e.g., the inner wall can be designed to act as the spring stop 160). Alternatively, for example, one or more pins, abutment walls, surfaces, etc. may be positioned within the handle to contact, and prevent deflection, of the spring.

In use, to properly position the location of the spring stop 160 to prevent further deflection of the spring 170, an acceptable amount of latch movement can be calculated based on the geometry of the latch 190 and broach 120 such that the latch 190 is prevented from moving from the second or engaged position to the first or released position when the lever 150 is in the second or closed position. In this manner, the latch 190 does not release the broach 120. Based on the latch movement calculation, the resulting compressed spring length can be calculated. With this length, calculations such as, for example, Finite Element Analysis, can be performed on the spring to find the amount of deflection in the direction of curvature based on the calculated compression. The amount of deflection can then be used to properly position the spring stop 160 so that the spring 170 contacts the spring stop 160 to limit additional deflection of the spring 170 and thus movement of the latch 190.

Thus arranged, as described herein, in accordance with one or more features of the present disclosure, an orthopedic broach 100 including a broach handle 140 with a four-bar linkage or coupling mechanism is disclosed. In one embodiment, the first link is a lever 150 used to actuate the linkage or coupling mechanism, the second link is a latch 190 to secure, hold, etc. the broach 120 to the handle 140, the third link is a spring 170 such as, for example, a flexible leaf spring, that is arranged and configured to bow in one direction based on its curvature (e.g., it deflects in the direction of the spring's curvature), and the four link is the broach handle frame 140.

In one embodiment, the linkage or coupling mechanism has an open bias position and a closed bias position. When the lever 150 is in the closed position, the broach 120 is held by the latch 190. The linkage or coupling mechanism is biased closed (e.g., spring 170 has passed through its shortest point and the force of the spring 170 is pushing the latch 190 to the closed position to engage the broach 120). With the linkage or coupling mechanism closed, if a force is applied to pull the broach from the broach handle, the latch will move and the spring will compress, causing it to bow in the direction of curvature. In accordance with one or more features of the present disclosure however, the spring 170 will contact, encounter, etc. a spring stop, a fixed surface, etc. 160 that prevents further bending, deflection, etc. of the spring 170. In use, the spring stop 160 is positioned such that the spring 170 contacts the spring stop 160 prior to the latch 190 releasing its hold on the broach 120.

It should be understood that it is envisioned that orientations of the link in the mechanism can vary, as can the direction of deflection. In addition, in various configurations, the spring can be any of the three-moving links in the mechanism, alternatively, the spring can be combined with the lever or latch.

Figure 7:
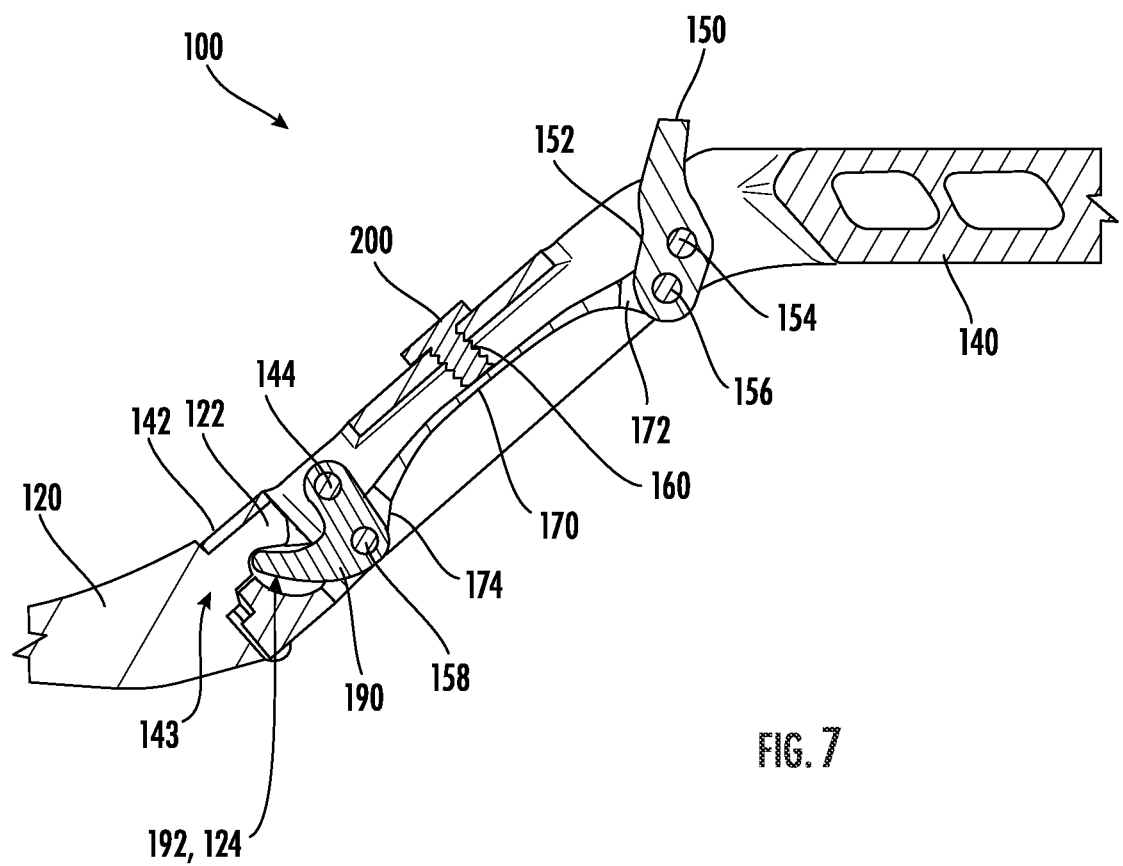
FIG. 7 is a detailed, cross-sectional view of an alternate example of an embodiment of a linkage or coupling mechanism for an orthopedic broach in accordance with one or more features of the present disclosure.

With reference to FIG. 7, an alternate embodiment of an orthopedic broach 100 in accordance with one or more features of the present disclosure is illustrated. In use, the orthopedic broach is substantially similar to the orthopedic broach previously described herein in connection with FIGS. 1-6 except as described herein. As illustrated, the orthopedic broach may include a movable or adjustable member such as, for example, a screw 200 arranged and configured to extend through an opening formed in the handle 140 and into contact with the spring 170. In use, the screw 200 may be adjusted (e.g., rotated) into more or less contact with the spring 170. As such, the movable or adjustable member (e.g., screw) 200 acts as an adjustable spring stop 160. Thus arranged, adjustments could be made to more precisely control the allowable deflection of the spring 170, or adjustments could be made to account for wear of the mechanism over time.

The foregoing description has broad application. Accordingly, the discussion of any embodiment is meant only to be explanatory and is not intended to suggest that the scope of the disclosure, including the claims, is limited to these example embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The term "a" or "an" entity, as used herein, refers to one or more of that entity. As such, the terms "a" (or "an"), "one or more" and "at least one" can be used interchangeably herein. The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein. The phrases "at least one", "one or more", and "and/or", as used herein, are open-ended expressions that are both conjunctive and disjunctive in operation.

All directional references (e.g., proximal, distal, upper, underside, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority but are used to distinguish one feature from another. The drawings are for purposes of illustration only and the dimensions, positions, order and relative sizes reflected in the drawings attached hereto may vary.

What is claimed is:

1. An orthopedic broach comprising:
   a cutting tip; and
   a handle including a lever, a spring, and a latch, the lever being moveably coupled to the handle between a first position and a second position, the latch being moveably coupled to handle between a released position and an engaged position, the spring coupling the lever to the latch so that movement of the lever from the first position to the second position moves the latch from the released position wherein the cutting tip can be inserted into the handle to the engaged position wherein the cutting tip is coupled to the latch;
   wherein the handle includes a stop member arranged and configured to contact the spring so that in the second position, the stop member contacts the spring to prevent further deflection of the spring to provide increased resistance against removal of the cutting tip from the latch.

2. The orthopedic broach of claim 1, wherein by preventing further deflection of the spring, the stop member increases a total resistance provided by the spring to prevent decoupling of the cutting tip from the handle when excessive forces are applied to the orthopedic broach.

3. The orthopedic broach of claim 1, wherein the stop member is arranged and configured as an inner wall of the handle.

4. The orthopedic broach of claim 1, wherein the stop member is arranged and configured as a screw arranged and configured to extend through an opening formed in the handle and into contact with the spring, rotation of the screw adjusting a deflection of the spring.

5. The orthopedic broach of claim 1, wherein the spring includes first and second ends, the first end is coupled to the lever, the second end is coupled to the latch.

6. The orthopedic broach of claim 1, wherein the cutting tip includes a connector portion at an end thereof, the connector portion including a recess arranged and configured to receive a tip of the latch.

7. The orthopedic broach of claim 6, wherein moving the lever from the first position to the second position causes the spring to move the latch into engagement with the recess formed in the connector portion of the cutting tip to secure the cutting tip to the handle.

8. The orthopedic broach of claim 7, wherein moving the lever from the first position to the second position causes the spring to deflect from a first unflexed position to a second flexed position, the stop member preventing the spring from completely flexing thereby providing an increased force onto the latch to prevent the latch from moving to the released position.

9. The orthopedic broach of claim 1, wherein the lever and the latch are pivotably coupled to the handle.

10. The orthopedic broach of claim 9, wherein the lever is pivotably coupled to the handle via a first pivot pin passing through the lever, the latch is pivotably coupled to the handle via a second pivot pin passing through the latch, the spring includes a first end and a second end, the first end of the spring is pivotably coupled to the lever by a third pivot pin, and the second end of the spring is pivotably coupled to the latch via a fourth pivot pin.

11. The orthopedic broach of claim 1, wherein, with the lever in the first position, the spring is in an unflexed position extending between the lever and the latch, and, with the lever in the second position, the spring transitions to a flexed position to exert an increased force onto the latch, the stop member preventing the spring from unflexing in the second position and thus preventing the latch from releasing the cutting tip.

12. An orthopedic broach comprising:
a cutting tip;
a handle including a lever, a linkage, and a latch, the lever being moveably coupled to the handle between a first position and a second position, the latch being moveably coupled to handle between a released position and an engaged position, the linkage coupling the lever to the latch so that movement of the lever from the first position to the second position moves the latch from the released position wherein the cutting tip can be inserted into the handle to the engaged position wherein the cutting tip is coupled to the latch; and
means for preventing the linkage from moving in the second position so that, in the second position, the latch is subjected to increased resistance from moving to prevent the cutting tip from being decoupled from the handle;
wherein:
the linkage is a spring arranged and configured to move between a first configuration and a second configuration, the spring comprising increased flexion in the second configuration;
movement of the lever from the first position to the second position, transitions the spring from the first configuration to the second configuration; and
the means for preventing the linkage from moving restricts an amount of flexion of the spring in the second configuration.

13. The orthopedic broach of claim 12, wherein the means for preventing the linkage from moving comprises a stop surface arranged and configured to contact the spring in the second position to restrict the amount of flexion of the spring.

14. The orthopedic broach of claim 13, wherein the stop member increases a total resistance provided by the spring to prevent decoupling of the cutting tip from the handle when excessive forces are applied to the orthopedic broach.

15. The orthopedic broach of claim 13, wherein the stop surface is arranged and configured as an inner wall of the handle.

16. The orthopedic broach of claim 12, wherein the cutting tip includes a connector portion at an end thereof, the connector portion including a recess arranged and configured to receive a tip of the latch.

17. The orthopedic broach of claim 12, wherein the lever and the latch are pivotably coupled to the handle.

18. The orthopedic broach of claim 17, wherein the lever is pivotably coupled to the handle via a first pivot pin passing through the lever, the latch is pivotably coupled to the handle via a second pivot pin passing through the latch, the linkage includes a first end and a second end, the first end of the linkage is pivotably coupled to the lever by a third pivot pin, and the second end of the linkage is pivotably coupled to the latch via a fourth pivot pin.

19. An orthopedic broach comprising:
a cutting tip;
a handle including a lever, a linkage, and a latch, the lever being moveably coupled to the handle between a first position and a second position, the latch being moveably coupled to handle between a released position and an engaged position, the linkage coupling the lever to the latch so that movement of the lever from the first position to the second position moves the latch from the released position wherein the cutting tip can be inserted into the handle to the engaged position wherein the cutting tip is coupled to the latch; and
means for preventing the linkage from moving in the second position so that, in the second position, the latch is subjected to increased resistance from moving to prevent the cutting tip from being decoupled from the handle;
wherein moving the lever from the first position to the second position causes the linkage to deflect from a first unflexed position to a second flexed position, the means for preventing the linkage from moving inhibiting the linkage from completely flexing thereby providing an increased force onto the latch to prevent the latch from moving to the released position.

20. An orthopedic broach comprising:
a cutting tip;
a handle including a lever, a linkage, and a latch, the lever being moveably coupled to the handle between a first position and a second position, the latch being moveably coupled to handle between a released position and an engaged position, the linkage coupling the lever to the latch so that movement of the lever from the first position to the second position moves the latch from the released position wherein the cutting tip can be inserted into the handle to the engaged position wherein the cutting tip is coupled to the latch; and
means for preventing the linkage from moving in the second position so that, in the second position, the latch is subjected to increased resistance from moving to prevent the cutting tip from being decoupled from the handle;
wherein the linkage is a leaf spring, and, with the lever in the first position, the spring is in an unflexed position extending between the lever and the latch, and, with the lever in the second position, the spring transitions to a flexed position to exert an increased force onto the latch, the means for preventing the linkage from moving being arranged and configured to prevent the spring from unflexing in the second position and thus preventing the latch from releasing the cutting tip.

* * * * *